United States Patent
Lee et al.

(10) Patent No.: US 7,974,454 B1
(45) Date of Patent: *Jul. 5, 2011

(54) CAPTURE CONTROL FOR IN VIVO CAMERA

(75) Inventors: Chung-Ta Lee, Sunnyvale, CA (US); Kang-Huai Wang, Saratoga, CA (US); Gordon C Wilson, San Francisco, CA (US)

(73) Assignee: Capso Vision Inc., Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/050,797

(22) Filed: Mar. 17, 2011

Related U.S. Application Data

(63) Continuation of application No. 12/776,434, filed on May 10, 2010, now Pat. No. 7,940,973.

(51) Int. Cl.
 *G06K 9/00* (2006.01)
(52) U.S. Cl. ......... 382/128; 382/236; 348/699; 348/700
(58) Field of Classification Search ............... 382/128
See application file for complete search history.

(56) References Cited

U.S. PATENT DOCUMENTS

| | | | | |
|---|---|---|---|---|
| 5,581,302 A * | 12/1996 | Ran et al. | ........ | 375/240.16 |
| 5,588,067 A * | 12/1996 | Peterson et al. | ........ | 382/103 |
| 6,480,225 B1 * | 11/2002 | Kim | ........ | 348/143 |
| 6,709,387 B1 * | 3/2004 | Glukhovsky et al. | ........ | 600/109 |
| 6,800,060 B2 * | 10/2004 | Marshall | ........ | 600/309 |
| 6,803,945 B1 * | 10/2004 | Needham | ........ | 348/207.1 |
| 6,936,003 B2 * | 8/2005 | Iddan | ........ | 600/114 |
| 6,939,292 B2 * | 9/2005 | Mizuno | ........ | 600/118 |
| 7,206,026 B2 * | 4/2007 | Hsiung et al. | ........ | 348/441 |
| 7,271,830 B2 * | 9/2007 | Robins et al. | ........ | 348/208.6 |
| 7,492,935 B2 * | 2/2009 | Glukhovsky | ........ | 382/128 |
| 7,526,028 B2 * | 4/2009 | Sung et al. | ........ | 375/240.16 |
| 7,643,056 B2 * | 1/2010 | Silsby | ........ | 348/155 |
| 7,792,344 B2 * | 9/2010 | Wang et al. | ........ | 382/128 |
| 7,796,870 B2 * | 9/2010 | Wang | ........ | 396/14 |
| 7,940,973 B2 * | 5/2011 | Lee et al. | ........ | 382/128 |
| 2003/0023150 A1 * | 1/2003 | Yokoi et al. | ........ | 600/300 |
| 2003/0202605 A1 * | 10/2003 | Hazra et al. | ........ | 375/240.26 |
| 2004/0174459 A1 * | 9/2004 | Holt et al. | ........ | 348/452 |
| 2005/0143624 A1 * | 6/2005 | Iddan | ........ | 600/112 |
| 2006/0155174 A1 * | 7/2006 | Glukhovsky et al. | ........ | 600/301 |
| 2006/0198443 A1 * | 9/2006 | Liang et al. | ........ | 375/240.16 |
| 2006/0293558 A1 * | 12/2006 | De Groen et al. | ........ | 600/101 |
| 2007/0098379 A1 * | 5/2007 | Wang et al. | ........ | 396/14 |
| 2007/0116119 A1 * | 5/2007 | Wang | ........ | 375/240.12 |
| 2008/0170846 A1 | 7/2008 | Wang | | |
| 2009/0299359 A1 * | 12/2009 | Swain | ........ | 606/27 |
| 2009/0322865 A1 * | 12/2009 | Wang et al. | ........ | 348/68 |

* cited by examiner

*Primary Examiner* — Sath V. Perungavoor
(74) *Attorney, Agent, or Firm* — Blairtech Solution LLC

(57) ABSTRACT

Systems and methods are provided for capture control of video data from a capsule camera system having an on-board storage or wireless transmission. The capsule camera system moves through the GI tract under the action of peristalsis and records images of the intestinal walls. For some periods of time, the capsule camera system may move very slowly and there are little differences in the image data between different frames. These frames can be designated for discard to conserve storage space or conserve power. A capsule control processing unit is incorporated to evaluate motion metric based on image data associated with a current frame and a previous frame. A decision is made based on a profile of the motion metric to select an operation mode from a group comprising Capture Mode and Conservation Mode. The capsule camera system is then operated according to the selected operation mode.

22 Claims, 15 Drawing Sheets

CAPTURE CONTROL FOR IN VIVO CAMERA

CROSS REFERENCE TO RELATED APPLICATIONS

The present invention is a continuation of and claims priority to the US Patent Application, entitled "Image Capture Control for In Vivo Camera", Ser. No. 12/776,434, filed on May 10, 2010, which is a continuation in part of US Patent Application, entitled "In Vivo Autonomous Camera with On-Board Data Storage or Digital Wireless Transmission in Regulatory Approved Band", Ser. No. 11/533,304, filed on Sep. 19, 2006, and US Patent Application, entitled "Lighting Control For In Vivo Capsule Camera", Ser. No. 11/623,601, filed on Jan. 16, 2007. These U.S. Non-Provisional Patent Applications are hereby incorporated by reference in their entireties.

FIELD OF THE INVENTION

The present invention relates to diagnostic imaging inside the human body. In particular, the present invention relates to controlling image capture of capsule camera having on-board storage or wireless transmission.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. This application describes a motion detection that is conducted using a portion of each image, the portion being stored in a partial frame buffer. In one embodiment, two partial frame buffers are used as operand buffers for a reduced version of a current image and a reference image, respectively. The reference frame buffer corresponds to the one containing a previously stored or transmitted digital image. When the image in the operand partial frame buffer is determined not to be stored, that partial frame buffer may be overwritten by the next digital image to be motion-detected. Otherwise, the operand partial frame buffer would be designated the next reference partial frame buffer, and the current reference partial frame buffer is designated the next operand partial frame buffers. In the above application, a metric for measuring the degree of motion between the two partial images described and is used to compare with a threshold as to whether to capture an underlying image or as to determine a proper compression ratio for the underlying image.

The U.S. patent application Ser. No. 11/623,601, entitled "Lighting Control for In Vivo Capsule Camera" describes methods and systems to adjust light source illumination based on image parameter evaluated for an image. Furthermore, the patent application discloses a motion detection circuit which compares the extracted parameter values in two images to detect motion of the capsule camera. The controller in the capsule camera system can be configured to operate the capsule camera in an active mode and a monitor mode according to the result of motion detection. However, the patent does not address adjusting the image sensor as additional capsule camera control to conserve storage and/or power consumption.

Another capsule camera system with on-board data storage or wireless transmission was disclosed in the U.S. patent application Ser. No. 12/543,508, entitled "Image Capture Control for in Vivo Autonomous Camera," filed on Aug. 19, 2009. This application describes an adaptive and dynamic method to adjust the parameter for image capture of a capsule camera with on-board image storage or wireless transmitter. A metric measuring the degree of motion is first computed from a partial frame of current image and a partial frame of a previously captured image. The metric is then compared against a set of parameters to determine a proper action for the underlying image.

While the applications mentioned above use motion detection and motion estimation to eliminate some unnecessary image capture and conserved the precious on-board storage and battery power, it may not fully address other aspects of camera capture control. For example, when there is no motion or little motion detected, images captured do not have to be in full spatial resolution. Furthermore, the luminous energy of the light source may also affect the quality of captured images and affect storage and power consumption requirements, where the luminous energy is represented as a product of the luminous intensity and the exposure time of the light source. It is the goal of the present invention to address these issues of capture control based on motion metric.

BRIEF SUMMARY OF THE INVENTION

The present invention provides a method and system for capsule camera control by providing a light source to illuminate lumen walls and receiving image data from an image sensor corresponding to a scene illuminated by the light source. The received image data are used for motion metric evaluation, wherein the motion metric evaluation is based on the image data associated with a current frame and a previous frame. A profile of the motion metric is used for determining an operation mode selected from a group comprising Capture Mode and Conservation Mode. According to the mode selected, corresponding light source control is then applied to the light source for a desired illumination needed for image capture. An optional image cropping/spatial sub-sampling module may be used to reduce image size for motion metric evaluation. A buffer memory may be used to buffer the image data for the current frame. If the Capture Mode is selected, the image data for the current frame can be stored in archival memory. In an alternative embodiment of the present capture control, an additional (N−1) frames may be captured, where N is an integer greater than 1. The light source control is applied to cause the light source to provide sufficient luminous energy to illuminate lumen walls, and the image data from the sensor is received and stored in the archival memory. The above procedure will be repeated (N−1) times. If the Conservation Mode is selected, the light source control will cause the luminous energy of the light source to be substantially reduced to conserve power, where substantially reducing the luminous energy includes a mode of turning off the light source, and/or the image sensor will be configured to cause partial frame output. The luminous energy of a light source can be controlled by adjusting the output light intensity, adjusting the exposure time, or a combination of both. The incoming image may be discarded, i.e., not stored. The Conservation Mode may be applied to M frames, wherein the M is an integer greater than or equal to zero. Instead of discarding the incoming image, the Conservation Mode may alternatively store the incoming image in low-quality using substantially reduced luminous energy and/or partial frames. The phase that the capture control processing module evaluates the motion metric and determines an operation mode is termed as Motion Assessment phase. When the processing corresponding to the Capture Mode or the Conservation Mode is completed, the capture control will return to the Motion Assessment phase and the process will iterate.

In another embodiment of the present invention, during the Motion Assessment phase, the image sensor is configured to cause partial frame output instead of using a processing module. In order to conserve system hardware resources, the image data for the current frame is not buffered in memory. If the Capture Mode is selected, the light source control and the image sensor control will be applied to cause images to be captured in good quality. In the Capture Mode, N frames will be captured where N is an integer greater than 0. If the Conservation Mode is selected, the light source control will be applied to cause the luminous energy of the light source to be substantially reduced and/or the image sensor can be configured to cause partial frame output or no frame output. The incoming image may be discarded, i.e., not stored. The Conservation Mode may be applied to M frames, wherein the M is an integer greater than or equal to zero. Instead of discarding the incoming image, the Conservation Mode may alternatively store the incoming image.

In an alternative embodiment according to the present capture control technique, the motion evaluation is performed using an external processing unit instead of a module inside the capsule camera, wherein the image data is transmitted to the external processing unit for motion metric evaluation. The external processing unit will also determine an operation mode based on a profile of the motion metric. The operation mode determined is then sent back to the capture control processing module and the capsule camera system will be operated according to the operation mode received.

A capsule camera apparatus according to an embodiment of the present invention is disclosed. The capsule camera apparatus comprises a light source coupled to receive a light source control to adjust light intensity, wherein a first light source control is applied; an image sensor coupled to an image buffer to provide image data; a motion evaluation module coupled to the image buffer to measure motion metric based on the image data associated with a current frame and a previous frame; and a decision module to select an operation mode based on a profile of the motion metric. Another camera apparatus according to an embodiment of the present invention is also disclosed. The capsule camera apparatus comprises a light source coupled to receive a light source control to adjust light intensity, wherein a first light source control is applied; an image sensor coupled to receive an image sensor control to adjust image sensor, wherein the image sensor is coupled to an image buffer to provide image data, wherein a first image sensor control is applied to the image sensor; a motion evaluation module coupled to the image buffer to measure motion metric based on the image data associated with a current frame and a previous frame; and a decision module to select an operation mode based on a profile of the motion metric.

The foregoing and other objects, features and advantages of the present invention will be apparent from the following detailed description of the preferred embodiments which make reference to several figures of the drawing.

DETAILED DESCRIPTION OF THE INVENTION

Figure 1A:
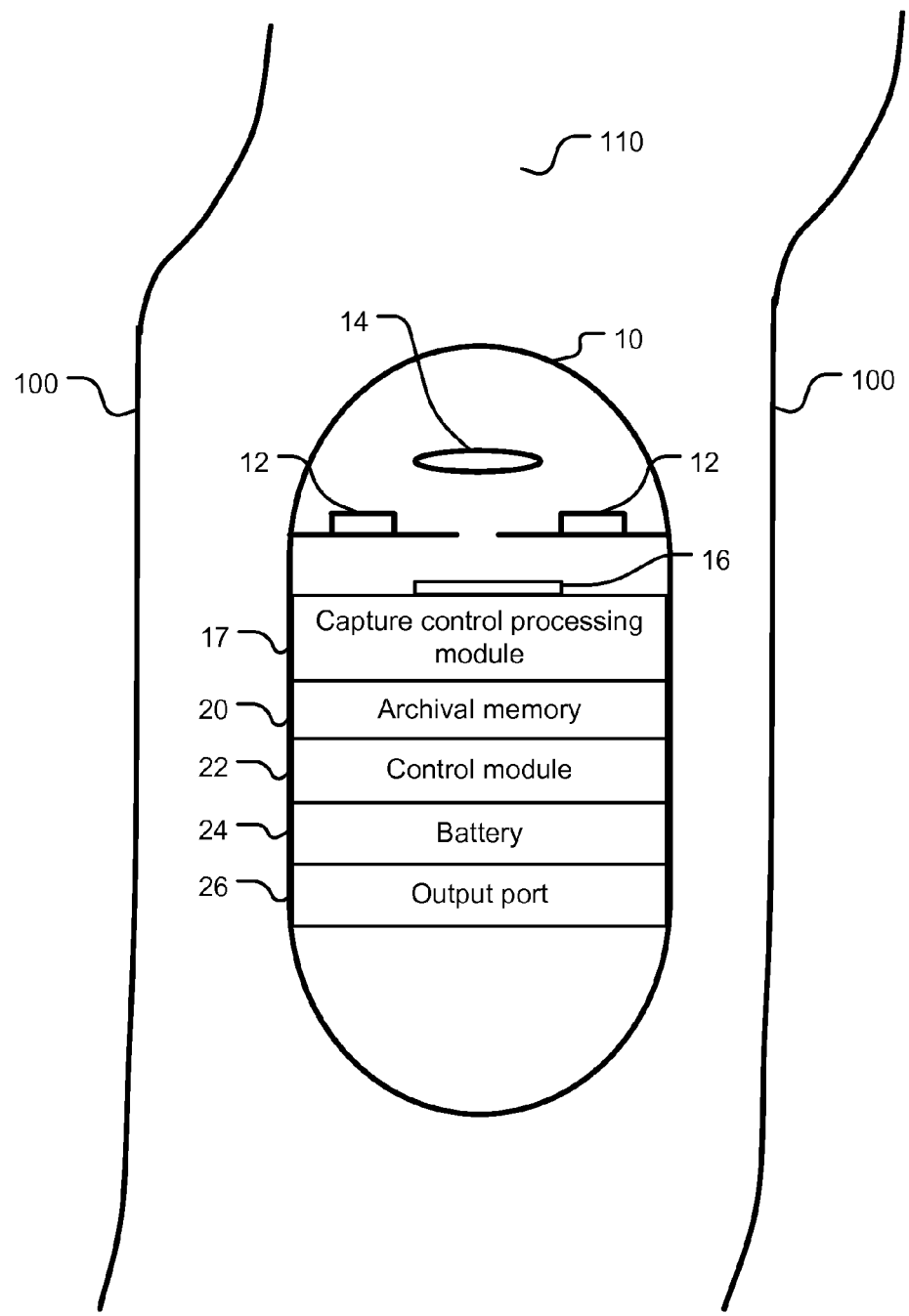
FIG. 1A illustrates one example of capsule camera system having on-board storage, according to one embodiment.

Semiconductor memories are low-cost, low-power, easily available from multiple sources, and compatible with application specific integrated circuit (ASIC) and sensor electronics (i.e., the data sources), and a personal computer (i.e., the data destination) without format conversion devices. One embodiment of the present invention allows images to be stored in an "on-board storage" using semiconductor memories. To enable storing a large number of diagnostic images in such areas as the colon, a method according to one embodiment evaluates motion metric between two frames. If the motion between the two frames is large enough, the image data is captured in higher quality by using a higher resolution and/or a larger picture size. Furthermore, the luminous energy of light source can also be used to control the storage size when an image compression method is used. In a typical image compression system, lower luminous energy will reduce the dynamic range of the captured image and consequently results in higher compression ratio. According to one embodiment, the system control takes advantage of the fact that, for some time, either the capsule moves very little in the GI tract, or the portion of the GI tract is within the camera's view is not changing. For such periods of time, the images need not be stored or the images can be stored in lesser quality to conserve storage space or power consumption. In this disclosure the terms "capsule" and "capsule camera" are inter-exchangeable. Also the terms "capsule system" and "capsule camera system" are inter-exchangeable.

As described in U.S. patent application Ser. No. 11/533,304 and U.S. patent application Ser. No. 12/543,508, motion evaluation can be utilized to dynamically control image capture. Nevertheless, motion evaluation itself will consume noticeable amount of power. In order to reduce the power consumption associated with motion metric computation, partial frame can be used. The partial frame can be derived from a full frame by spatially reducing the image size, which can be spatial sub-sampling and/or spatial clopping. The use of partial frame not only reduces power consumption associated with motion metric computation, but also reduces the storage size required for buffering the image data. Some image sensors offer a control mechanism to output image data at reduced size. For example, a set of programmable registers may be used to select region of interest (ROI), where the location of a starting pixel, horizontal size and vertical size of picture can be selected. The use of ROI effectively achieves image clopping. Often, the image sensor also offers spatial sub-sampling feature where separate horizontal and vertical sub-sampling ratios may be used. Usually there is a set of registers which can be programmed to select one of desired spatial sub-sampling ratios. For example, a 2:1 vertical sub-sampling ratio and a 4:1 horizontal sub-sampling ratio will result in a picture size equal to ⅛ of the original size. In the case that the image sensor does not support image sensor control to adjust the output image size, a separate processing unit may be used to perform spatial sub-sampling and cropping.

The luminous energy of light source can serve as another parameter for capture control. When motion metric evaluated is small, the associated frame do not need to be stored or can be stored at lower quality. If a frame is captured at reduced luminous energy, the captured image will have reduced intensity range which will likely result in smaller compressed file size than an image having full intensity range. In addition, reducing the luminous energy will also reduce power consumption. In a capsule camera system, multiple light sources may be used to illuminate lumen walls. The luminous energy can be adjusted by tuning On/Off individual light sources. The luminous energy can also be controlled by adjusted the voltage or current provided to the light source or the exposure time, or a combination of both. For example, if LEDs are used as the light source, the electricity current supplied to the LEDs can be adjusted to control the light intensity of the LED. Alternatively, the exposure time of the light source can be reduced to lower the luminous energy. Some light sources may rely on supply voltage to adjust the intensity. In this disclosure, the luminous energy adjustment by tuning On/Off individual light sources is considered as a special case of multiplicative luminance control having a multiplicative factor of 0. The light source control circuits are well known in the art. Therefore, the schematic or block diagram associated with the light source control will not be shown in order not to obscure the inventions in unnecessary detail.

In one embodiment of the present capture control method, motion metric is evaluated based on images at reduced size and/or reduced luminous energy in order to conserve power consumption. Motion assessment is required in order to determine whether an image should be captured. The reduced image size and/or reduced luminous energy should be sufficient to evaluate motion metric while conserving power consumption required for computing the motion metric. According to the motion metric evaluated, the camera capture control may determine whether to capture the image and determine the quality of the image to be captured. For example, if there are substantial differences between a current frame and a reference frame as indicated by the motion metrics, the camera capture control may desire full image quality capture by using full spatial resolution and full luminous energy. On the other hand, if there are very little differences between a current frame and a reference frame as indicated by the motion metric, the camera capture control may determine to discard the image or store the image in lower quality by using lower spatial resolution and/or lower luminous energy.

The flow of the capture control may comprise a Motion Assessment phase to evaluate motion metric and determine whether to retain a good quality (Capture Mode) image or disregard the image (Conservation Mode) according to a profile of the evaluated motion metric. As one example, the Capture Mode may cause a full resolution image to be stored in an internal archival memory or in an external storage by transmitting the image to an external device. The Conservation Mode may cause the capsule camera to disregard following M frames by substantially reducing the luminous energy of the light source or turning off the light source. Alternatively, the Conservation Mode may store the M frames with substantially reduced luminous energy or with the light source turned off. Furthermore, in the case that the image sensor can be controlled by image sensor control to vary the output image size, the Conservation Mode may store these M frames with substantially reduced image size to conserve storage space. These low-quality M frames may be used for secondary viewing purposes such as to visually preview the contents. The operation modes determined for the sequence of images will provide useful information during playback. Therefore, the operation modes can be stored with the capture image data or stored separately. The M frames may also be discarded and not stored. The image sensor control may configure the sensor to not output image data, or the image data may be output from the se The motion metric evaluation may involve very extensive computations and consume high power. This is particularly true for motion metric evaluation based on a motion estimation method. Therefore, an external processing unit may be used to evaluate motion metric, where the power consumption usually is less of a concern for the external device than the capsule camera. When an external processing unit is used to evaluate motion metric, the image data has to be transmitted to the external processing unit for motion metric evaluation. The transmission of image data based on digital wireless communication in a regulatory approved band is known in the art and can be used for such purpose. Alternatively, the human body may be used as transmission medium to transmit the image data from inside the body to outside the body. One such technique is disclosed in the Patent Application Publication, serial number US 2003/0092973, entitled "Method and Apparatus for Communication between inside and outside of transmission medium using transmission medium as a communication line", published on May 15, 2003. In this disclosure, the term wireless transmission includes radio frequency transmission and electrical conduction through the human body. The image data transmitted for motion metric evaluation may correspond to partial frame in order to reduce the transmission bandwidth requirement as well as the transmission power.

In the disclosure, various embodiments and examples of the methods and structures mentioned above are described. It will be realized that this detailed description is illustrative only and is not intended to be in any way limiting. Other embodiments will readily suggest themselves to persons of ordinary skill in the art having the benefit of this disclosure.

FIG. 1A shows a swallowable capsule system 110 inside body lumen 100, in accordance with one embodiment. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 100 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is made of non-toxic material, and is sufficiently smooth to minimize the chance of lodging within the lumen.

As shown in FIG. 1A, capsule system 110 includes illuminating system 12 and a camera that includes optical system 14 and image sensor 16. An image captured by image sensor 16 is processed by capture control processing module 17 to determine the motion metric of the image within the optical view of the camera corresponding to a current frame and a previous frame. The capture control processing module 17 may be implemented in software that runs on a digital signal processor (DSP) or a central processing unit (CPU), in dedicated hardware, or a combination of both software and hardware. A semiconductor nonvolatile archival memory 20 may be provided to allow the images to be stored on-board and retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1A, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. The control module 22 may be responsible for controlling the overall system operation such as initial system turn-on and final image data retrieval. While the capture control processing module 17 and the control module 22 are shown as two separate modules, they may be integrated into one processing unit, they may share some common elements, or they may function collaboratively. For example, the decision for controlling the luminous energy of the LEDs may be provided by the capture control processing module 17, the control module 22 may contain the interface to provide the control signal to the LEDs to control the luminous energy.

The capture control processing module 17 selects an incoming image to retain only when there are enough differences between a current frame and a previous frame in order to conserve the limited storage space. The images are stored in the on-board archival memory system 20. The output port 26 shown in FIG. 1A is not operational in vivo but uploads data to a work station after the capsule is recovered, having passed from the body. The capture control processing module 17 comprises a module that computes a metric of motion. Depending on the amount of motion as indicated by the motion metric, the capture control processing unit 17 will determine if the underlying image should be captured, i.e., stored in the on-board storage or transmitted to external storage. If the amount of motion is small so that the differences between the underlying image and a previously captured image are small, the underlying image may not be needed to store, i.e., the underlying image is not captured. Alternatively, a low-quality image may be stored if the amount of motion is small.

Archival memory system 20 can be implemented by one or more nonvolatile semiconductor memory devices. There are numerous memory types that can be used; even photographic films can be used for image sensing and storage. Since the image data are digitized for digital image processing techniques, such as motion detection, memory technologies that are compatible with digital data are selected. Of course, semiconductor memories mass-produced using planar technology is the most convenient. Such memories are low-cost and may be obtained from multiple sources. Semiconductor memories are most compatible because they share common power supply with the sensors and other circuits in capsule system 110, and require little or no data conversion when interfaced with an upload device at output port 26. Archival memory system 20 preserves the data collected during the operation, after the operation while the capsule is in the body, and after the capsule has left the body, up to the time the data is uploaded. This period of time is generally less than a few days. A nonvolatile memory is preferred because data is held without power consumption, even after the capsule's battery power has been exhausted. Suitable non-volatile memory includes flash memories, write-once memories, or program-once-read-once memories. Alternatively, archival memory system 20 may be volatile and static (e.g., a static random access memory (SRAM) or its variants, such as VSRAM, PSRAM Archival memory 20 may be used to hold any initialization information (e.g., boot-up code and initial register values) to begin the operations of capsule system 110. The cost of a second non-volatile or flash memory may therefore be saved. That portion of the non-volatile can also be written over during operation to store the selected captured images. After the capsule passes from the body, it is retrieved. Capsule housing 10 is opened and input port 16 is connected to an upload device for transferring data to a computer workstation for storage and analysis.

Figure 1B:
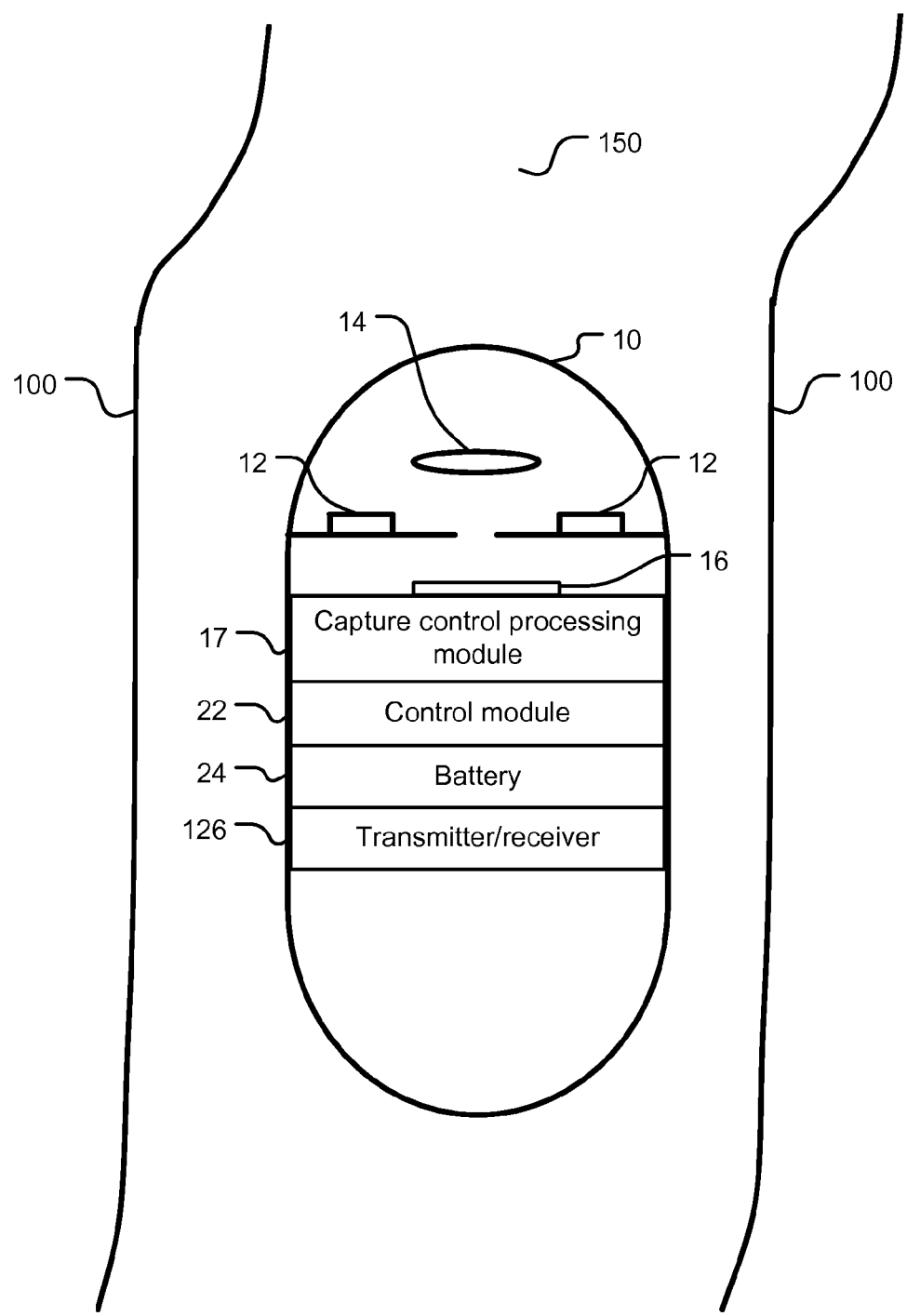
FIG. 1B illustrates one example of schematically capsule camera system having wireless transmitter/receiver, according to another embodiment.

FIG. 1B depicts an alternative capsule camera system 150 inside body lumen 100, in accordance with one embodiment. The capsule camera system in FIG. 1B is similar to that in FIG. 1A except that a transmitter/receiver 126 is used instead of an archival memory 20. In FIG. 1B, the same element as that in FIG. 1A is designated with the same reference numeral. While images captured are stored in the archival memory 20 in FIG. 1A, images captured are transmitted by the transmitter/receiver 126 in FIG. 1B to an external device for storage. The external device may be a base-station. The transmitter/receiver 126 may receive signals from the external device. As to be discussed later, the transmitter/receiver 126 may also be used to transmit image data to the external device for motion metric evaluation and to receive operation modes from the external device. In such example, the capsule camera system may also contain the archival memory 20 to store captured images and relies on the external processing unit to evaluate motion metric only. In this case, image data transmitted from the capsule camera system to the external processing unit is just for motion metric evaluation purpose.

Figure 2:
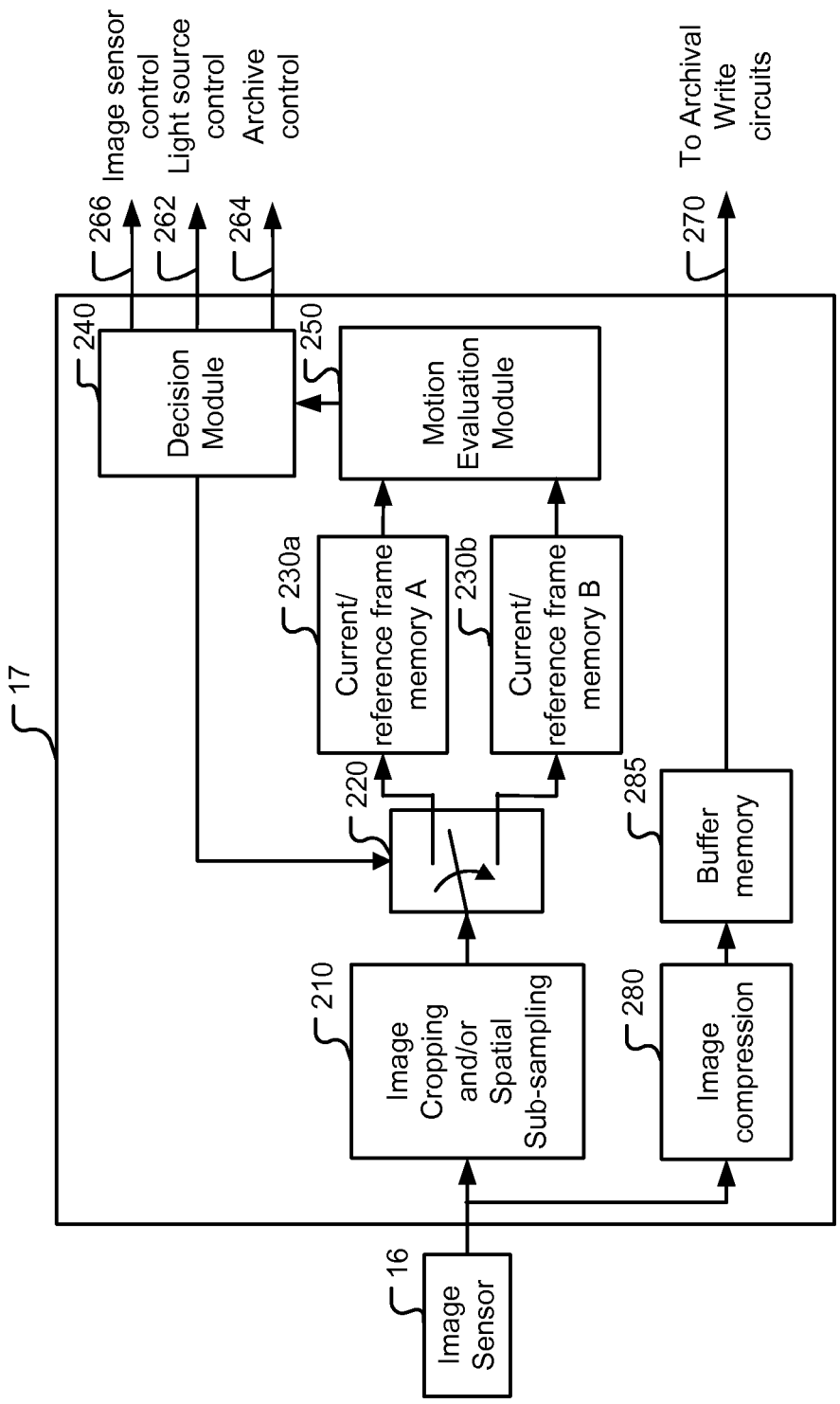
FIG. 2 illustrates an exemplary block diagram of the capture control processing module according to one embodiment, wherein an image cropping/spatial sub-sampling module is used.

FIG. 2 illustrates an example of capsule control processing module 17 according to one embodiment. The received image data is processed by the optional image cropping/spatial sub-sampling module 210 to reduce the image size of the image data from the image sensor 16. The use of the image cropping/spatial sub-sampling module 210 can reduce image size and consequently reduce the computational requirements for evaluating the motion metric. The image cropping/spatial sub-sampling module 210 may apply spatial sub-sampling to reduce the image size of the incoming data. For example, a 2:1 sub-sampling can be applied horizontally and vertically to reduce the image data to ¼ of its original size. Alternatively, the image size can also be reduced by cropping. For example, the central ¼ portion can be retained after cropping for motion metric evaluation. A combination of spatial sub-sampling and cropping can also be used to reduce the image size. While the image cropping/spatial sub-sampling module 210 can help to reduce the computational requirements for motion metric evaluation, the image cropping/spatial sub-sampling module 210 is not required to practice the present invention. The use of the image cropping/spatial sub-sampling module 210 is optional because motion evaluation cam also be based on full-size image data. After the optional cropping/spatial sub-sampling, the image is then stored in one of two frame memories 230a and 230b via the switch 220 and the other one of frame memories 230a and 230b contains a reference image, which is a previously stored image. The motion evaluation module 250 receives the two images from frame memories 230a and 230b and evaluates motion metric accordingly.

The motion evaluation can be based on a motion detection algorithm or a motion estimation algorithm. Motion detection and motion estimation are well known in the field. There are a variety of motion estimation and motion detection algorithms in the literature. For example, there is a class of block based motion estimation algorithm to estimate the motion vector for each block, and many fast algorithms for efficient computation of the motion vector have been reported in the literature. There is also a class of global motion estimation algorithm that estimates the dominant global vector for the while image. While motion estimation provides more detailed description of the differences between two images, motion estimation usually involves complex computations. On the other hand, motion detection measures motion metric in order to determine whether there are significant differences between the two images. Usually there is no need to determine the amount of movement between the two images and consequently motion detection requires less computation. Motion detection can be based on the sum of absolute differences (SAD) of frame differences, mean squared error (MSE) of frame differences, count of pixels having difference larger than a threshold, and count of zero-valued motion vector. The motion metric can be associated with computed motion vectors, global motion vector, SAD, MSE, count of pixels having large differences and count of zero-valued motion vectors.

The motion metric evaluated is then provided to the decision module 240 to decide an operation mode. For example, according to a profile of the motion metric, the decision module will choose either Capture Mode or Conservation Mode. The Capture Mode is selected when the motion metric is larger than a threshold and otherwise, the Conservation Mode is selected. While the Capture Mode and the Conservation Mode are used as an example, other operation modes may also be used to practice the present invention. For example, an additional Low-Quality Capture Mode may be used that retains image at low quality if the motion metric is between a lower threshold and a higher threshold. For the Capture Mode, the capture control processing module 17 will cause an image stored in the archival memory 20. The decision module 240 will provide light source control 262 to the light source, i.e., LEDs in this example, to cause the light source to produce sufficient luminous energy for image capture. The decision module 240 will also provide image sensor control signal 266 to the image sensor to operate the image sensor and synchronize the operation with the light source. Furthermore, the decision module 240 will also provide necessary archive control signal 264 to cause the image to be stored in the archival memory 20. The decision module 240 also controls the switch 220 so that the incoming image data will be written into an intended frame memory 230a or 230b. If the decision module 240 selects the Capture Mode, the image data in the current frame memory will be designated as a new reference frame memory. At the same time, the reference frame memory will be designated as a new current frame memory to receive the next incoming image.

A data path to archival memory is shown from the incoming image data, through image compression 280 and buffering memory 285 to archival write control 270. The incoming image data to be stored may be subject to optional image compression 280, such as the JPEG standard, to conservation storage space. The buffer memory 285 is used to buffer the image data. The output of the buffering memory 270 is provided to the archival memory through archival write circuit. The archival write circuit is coupled to the archive control signal 264 so that an image intended to be stored will be properly stored in the archival memory 20. While the buffer memory 285 is illustrated as an explicit block, it may also be embedded inside system memory inside the capsule camera. The size requirement of the buffer memory 285 depends on how the capsule camera is operated. In one example, the motion evaluation module 250 makes a decision based on image data corresponding to the current frame and a previous frame. The decision module 240 may determine to capture the current frame. In this case, the entire current frame has to be buffered, compressed or un-compressed, in the buffer memory 285. In another example, the decision to capture a frame can be made to the next incoming frame, i.e., a decision delayed by one frame. In this case, the incoming image data only needs to be slightly buffered before it is written into the archival memory. When compression such as JPEG is used, only a few line buffers will be needed inside the image compression 280, and the buffer memory 285 may only need to hold an amount of compressed data so that the compressed data can be properly written to the archival memory. The decision module 240 selects an operation mode may be based on a current motion metric and multiple previous motion metrics, instead of the current motion metric only. The current motion metric along with at least one previous motion metric constitute a profile of the motion metric. Very often, the motion metric data is correlated, i.e. neighboring motion metrics may have similar trend. For example, several consecutive small motion metrics may indicate that the capsule camera system is in a period of no movement or very little movement. Therefore, the decision module 240 may decide to discard more frames in this situation. The use of "a profile of motion metric" helps the decision module to make better decision.

FIG. 2 illustrates an example according to one embodiment of the present invention where separate blocks are shown for frame memory A 230a and B 230b, and buffer memory 285. However, it is known for skilled person in the art that the above mentioned frame memory A and B, and buffer memory may all reside in a memory device such as DRAM (Dynamic Random Access Memory) or SRAM (Static Random Access Memory) in the capsule camera. These separate blocks are used in FIG. 2 to illustrate the functional aspect of these buffer or memory. Furthermore, the buffer memory 285 may be also the same as for frame memory A 230a and B 230b if the reference frame memory can satisfy the requirement of buffering the image data to be archived.

Figure 3:
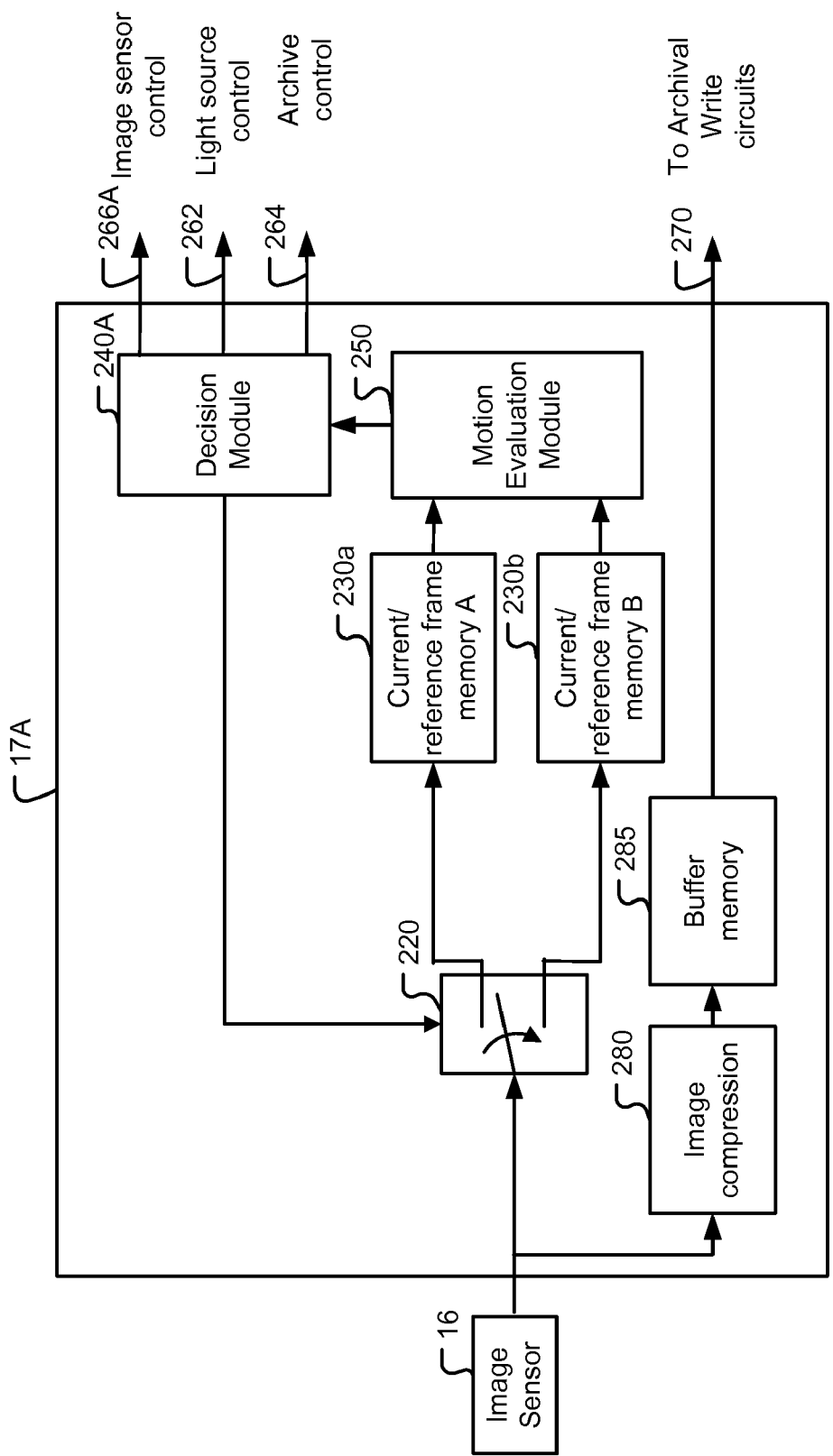
FIG. 3 illustrates another exemplary block diagram of the capture control processing module according to one embodiment, wherein the image sensor can adjust output image size according to the image sensor control.

FIG. 3 illustrates an example of alternative capsule control processing module 17A according to another embodiment. The capsule control processing module 17A is substantially the same as the capsule control processing module 17 except that the image cropping/spatial sub-sampling module 210 is not used in FIG. 3. The selection of a desired image size usually is provided by a set of control registers in image sensor 16. For example, a set of registers may be provided to select the horizontal sub-sampling ratio, the vertical sub-sampling ratio, and starting location and horizontal/vertical sizes for region of interest (ROI). The use of ROI effectively crops the image outside the ROI. Therefore, instead of using the image cropping/spatial sub-sampling module 210, some image sensors provide the same function by programming the corresponding registers.

The decision module 240A in FIG. 3 is similar to the decision module 240 in FIG. 2 except that the decision 240A also outputs image sensor control signal 266A, which includes needed information to control the output image size of the image sensor. The image sensor control signal 266A is coupled to the image sensor for controlling the operation. For example, at the Motion Assessment phase, the image sensor may be programmed to provide partial image data to reduce computational requirement for motion metric evaluation. As an illustration, the registers of the image sensor may be programmed for 2:1 vertical sub-sampling, 2:1 horizontal sub-sampling, and a central ROI having ½ horizontal size and ½ vertical size. This will result in an output image that is 1/16 of the full-size image. In the Capture Mode, the decision module 240A may provide image sensor control signal 266A to cause the image sensor to output a full-size as desired. In the Conservation Mode, there is no need to store the image. Alternatively, low-quality images may be stored for visual confirmation or other purposes. The luminous energy will be substantially reduced, which includes turning off the light source in the Conservation Mode. In addition, the image sensor can be programmed to provide an output image with substantially reduced size or no image output at all in the Conservation Mode. For example, the image sensor can be programmed to provide an output image at 1/64 of the full size to conserve power associated with image sensor operation and storage space. When a partial frame is used for motion evaluation in the system shown in FIG. 3, a full-size image corresponding to the current frame will not be available. Consequently, the capture decision made in the system of FIG. 3 will have to be applied to the next frame, i.e., the decision made is applied in a one-frame delay fashion.

Figure 4A:
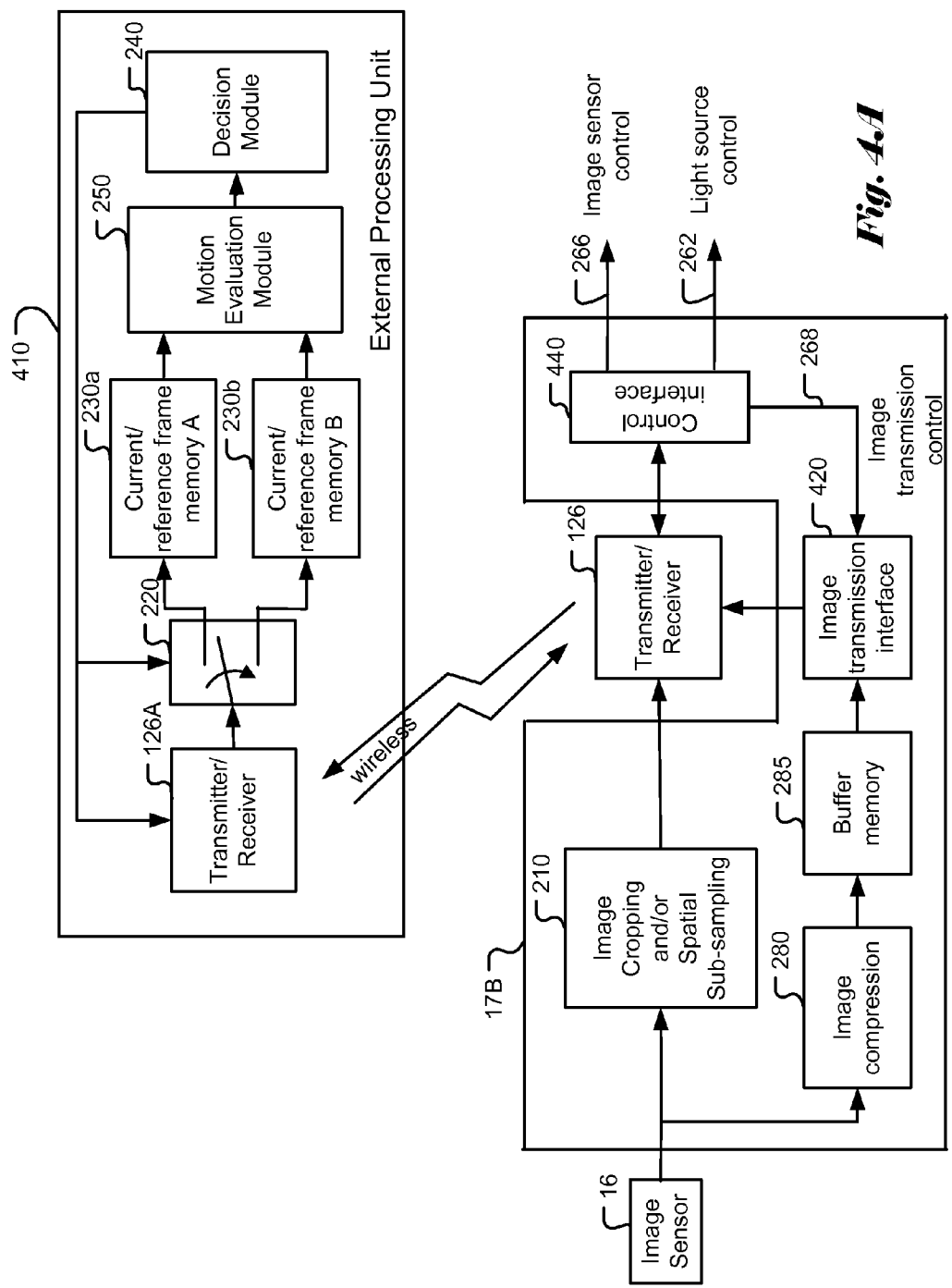
FIG. 4A illustrates an exemplary block diagram of the capture control processing module according to one embodiment, wherein an image cropping/spatial sub-sampling module is used and the motion evaluation is done by an external processing unit.

FIG. 4A illustrates another example of capsule control processing module 17B according to one embodiment. The capsule control processing module 17B is substantially the same as the capsule control processing module 17 in FIG. 2 except that the motion metric evaluation is performed externally. Instead of feeding into one of the frame memories 230a and 230b, the size-reduced image processed by the image cropping/spatial sub-sampling module 210 is transmitted by the transmitter/receiver 126 to an external processing unit 410. The external processing module 410 receives the image data from the transmitter/receiver 126A and feeds the image data to one of the frame memories 230a and 230b. The functions of the motion evaluation module 250 and decision module 240 are the same as these in FIG. 2. The decision module 240 selects the Capture Mode or the Conservation Mode according to a profile of the motion metric. Corresponding light source control, image sensor control and archive control are provided by the decision module to facilitate the selected mode. The light source control signal, image sensor control signal and the archive control signal from the decision module 240 are provided to the transmitter/receiver 126A to send to capture control processing module 17B of the capsule camera. The light source control signal, image sensor control signal and the archive control signal are received by the transmitter/receiver 126 of the capsule camera. The signals are then extracted and provided to the control interface 440. The control interface then applies the light source control signal 262 to control luminous energy of the light source and the image sensor control signal 266 to the image sensor. FIG. 4A illustrates an example of image archive outside the capsule camera. The incoming image to be stored may be compressed by the image compression module 280 and buffered by buffering memory 285 before it is provided to the image transmission interface 420. The image is then transmitted by the transmitter/receiver 126 to the external processing unit, which is located at the base-station. The transmitter/receiver 126A receives the image and provides it to archive storage, which is not shown in FIG. 4A. The archive control signal received by the control interface 440 is used as the image transmission control signal 268 to control the image transmission for archive.

Figure 4B:
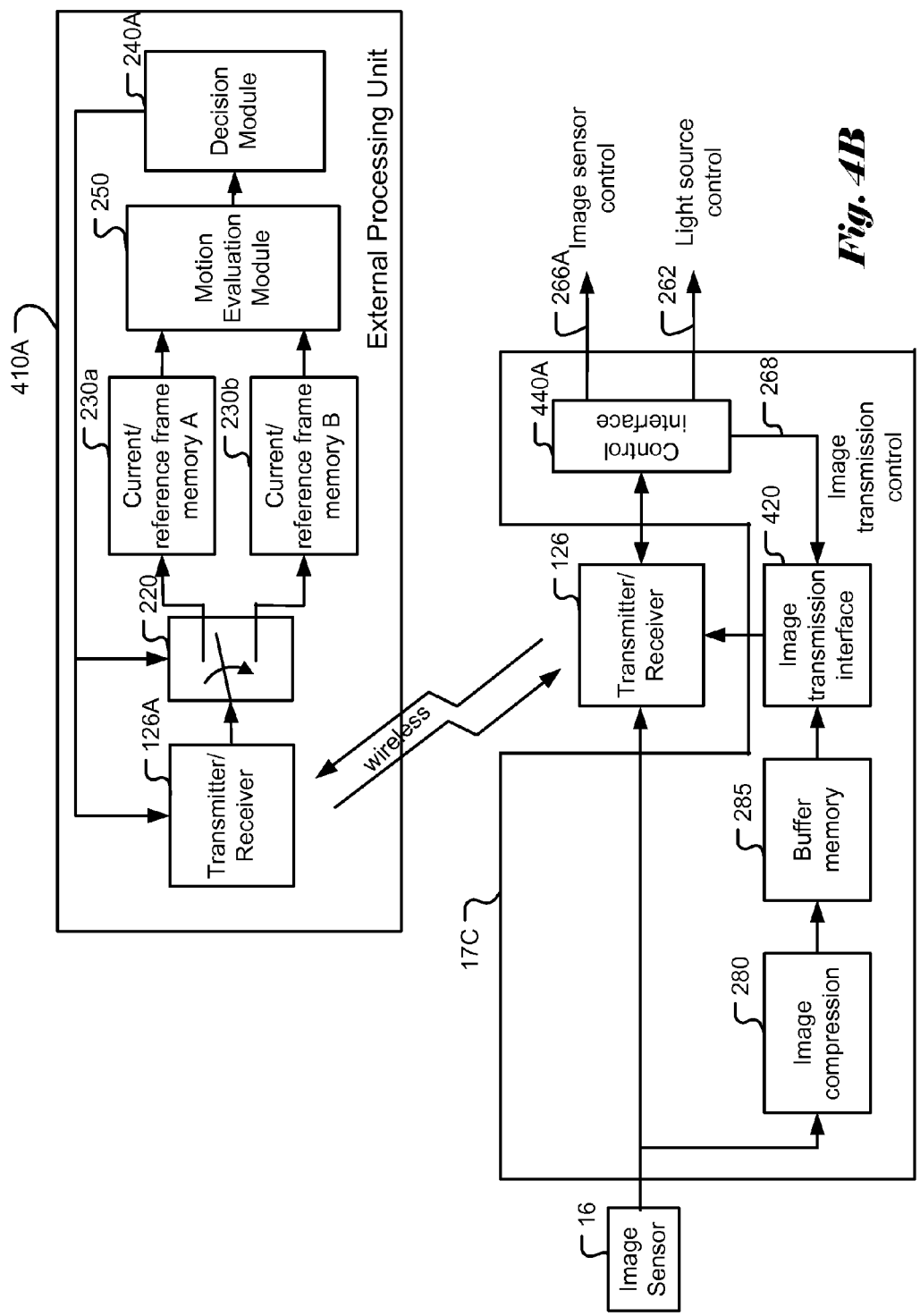
FIG. 4B illustrates another exemplary block diagram of the capture control processing module according to one embodiment, wherein the image sensor can adjust output image size based on the image sensor control and the motion evaluation is done by an external processing unit.

FIG. 4B illustrates yet another example of capsule control processing module 17C according to one embodiment. The capsule control processing module 17C is substantially the same as the capsule control processing module 17B except that image size reduction is performed by programming the image sensor control instead of the image cropping/spatial sub-sampling module 210. The decision module 240A selects the Capture Mode or the Conservation Mode according to a profile of the motion metric. Corresponding image sensor control, light source control, and archive control are provided by the decision module to facilitate the selected mode. The control signals are transmitted by the transmitter/receiver 126A in the external processing unit 410 to the transmitter/receiver 126 in the capsule camera. The control interface 440A applies the respective control signals to facilitate the selected operation mode. While FIG. 4A and FIG. 4B illustrate examples of embodiments where captured images are archived in an external storage at the base-station, on-board archival memory may also be used to store the captured images inside the capsule camera for later retrieval.

Figure 5:
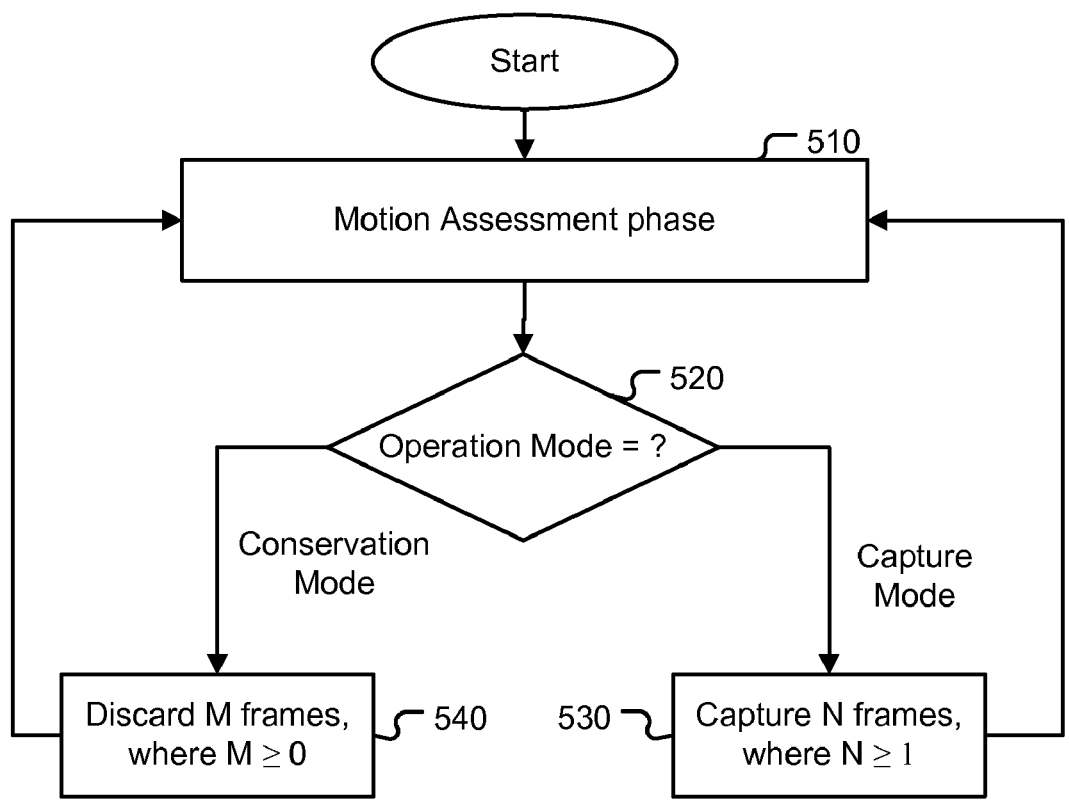
FIG. 5 is a flow chart illustrating the capture control operation to provide Capture Mode and Conservation Mode according to one embodiment.

FIG. 5 illustrates an example of high level operation flowchart according to one embodiment. The Motion Assessment phase 510 corresponds to a phase that the capture control processing module receives an incoming image and evaluates motion metric based on the current frame and a previous frame to determine an operation mode 520 selected from a group comprising Capture Mode 530 and Conservation Mode 540. The capsule camera system is then operated in the selected mode. When the operation of the select mode is completed, the capsule control processing module goes to the Motion Assessment phase again and the process iterates. While Capture Mode and Conservation Mode are used in this example, more modes may be included. For example, a Low-Quality Capture Mode may also be use that causes images captured with reduced quality. The Low-Quality Capture Mode may be used for motion metric between a low threshold and a high threshold. In one embodiment, the Low-Quality Capture Mode is treated as an alternative to discarding image in the Conservation Mode. Consequently, the Conservation Mode may cause the incoming image not to be stored or stored in low-quality. Furthermore, the configuration of the Motion Assessment phase can be dynamically changed. For example, different image sensor control or different light source control can be configured for returns from the Capture Mode and the Conservation Mode.

Figure 6A:
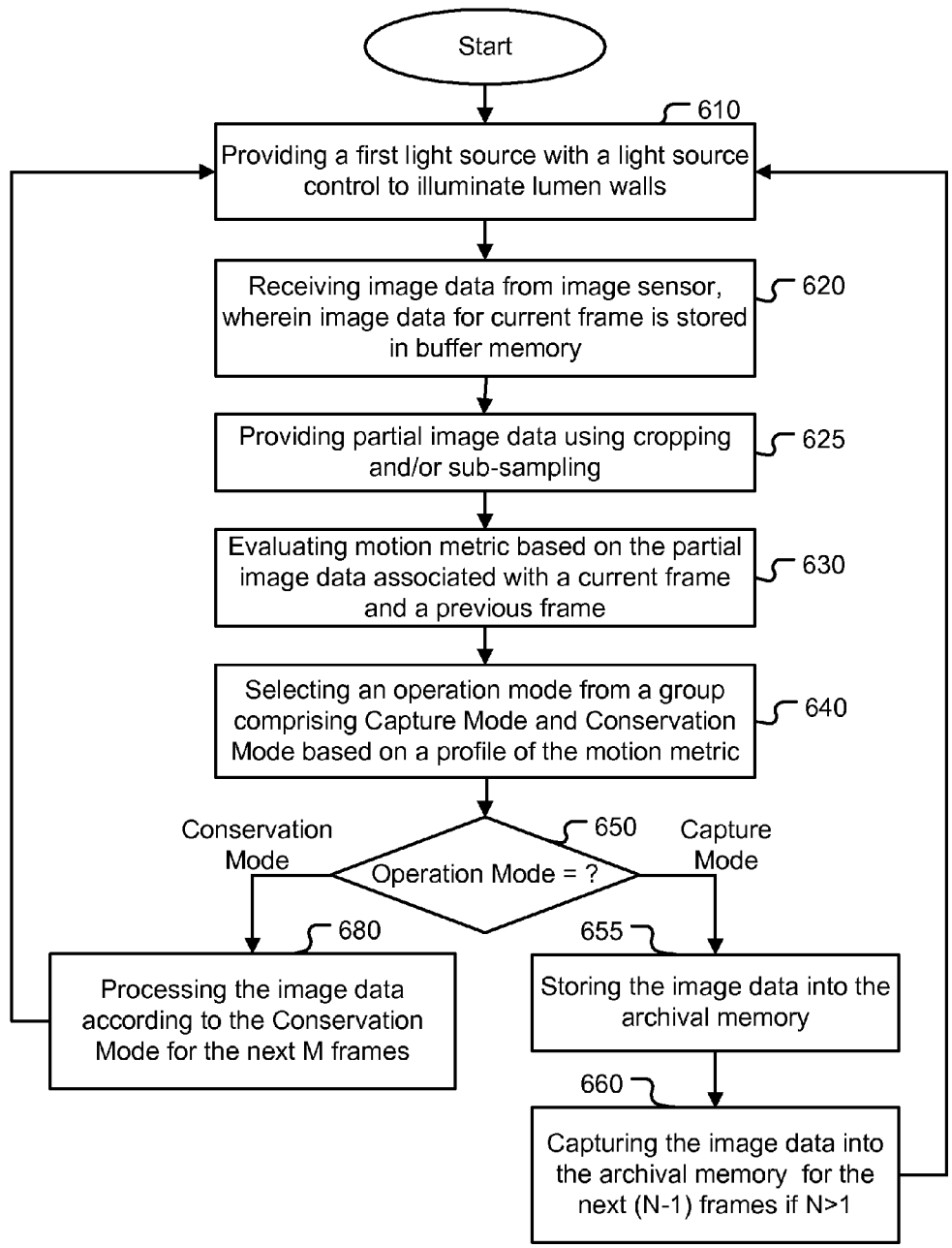
FIG. 6A is a flow chart illustrating an example of capture control operation according to one embodiment, wherein an image cropping/spatial sub-sampling module is used.

FIG. 6A illustrates a detailed exemplary flowchart for the operation of capsule control processing module 17 in FIG. 2. The steps 610 through 640 correspond to the Motion Assessment Mode 510 in FIG. 5. In order to assess motion metric, a first light source control is applied to the light source to illuminate lumen walls in step 610. The image data from the image sensor in then received and the image data is also buffered in buffer memory in step 620. Step 625 provides optional processing to produce a copy of the image with reduced image size by cropping and/or spatial sub-sampling the incoming image in order to reduce computational requirements. The original full-size image may be retained in buffer memory for possible archival storage. As mentioned previously, step 625 is optional since motion evaluation can also be performed based on full-size image data. In step 630, the motion metric is evaluated based on the partial image data associated with a current frame and a reference frame. The computed motion metric along with previous motion metrics are used to determine an operation mode in step 640. The mode is checked in step 650 to determine which branch the flow will follow. If the mode is the Capture Mode, the image data that is already in the buffer memory can be stored in the archival memory. If additional (N−1) frames are to be captured, where N is an integer greater than 1, the capture route 660 will be performed. If the mode is Conservation mode, the routine 680 is performed to process M frames, where M is an integer greater than or equal to zero. The image data that is already in the buffer memory at the beginning of conservation mode can be stored in the archival memory, if desired.

Figure 6B:
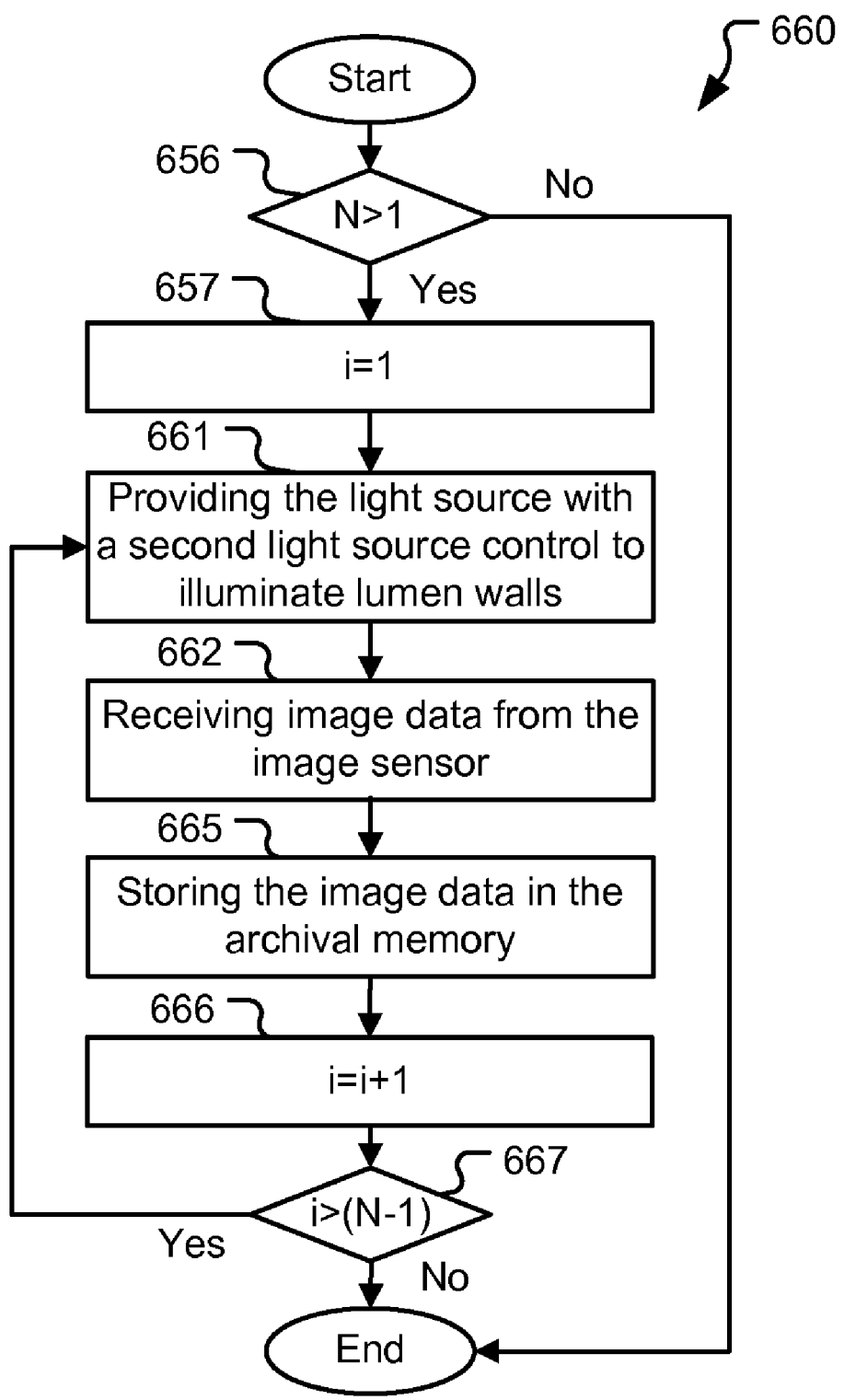
FIG. 6B is a flow chart illustrating an example of routine for capturing additional (N−1) frames in the Capture Mode according to one embodiment, where N>1.
Figure 6C:
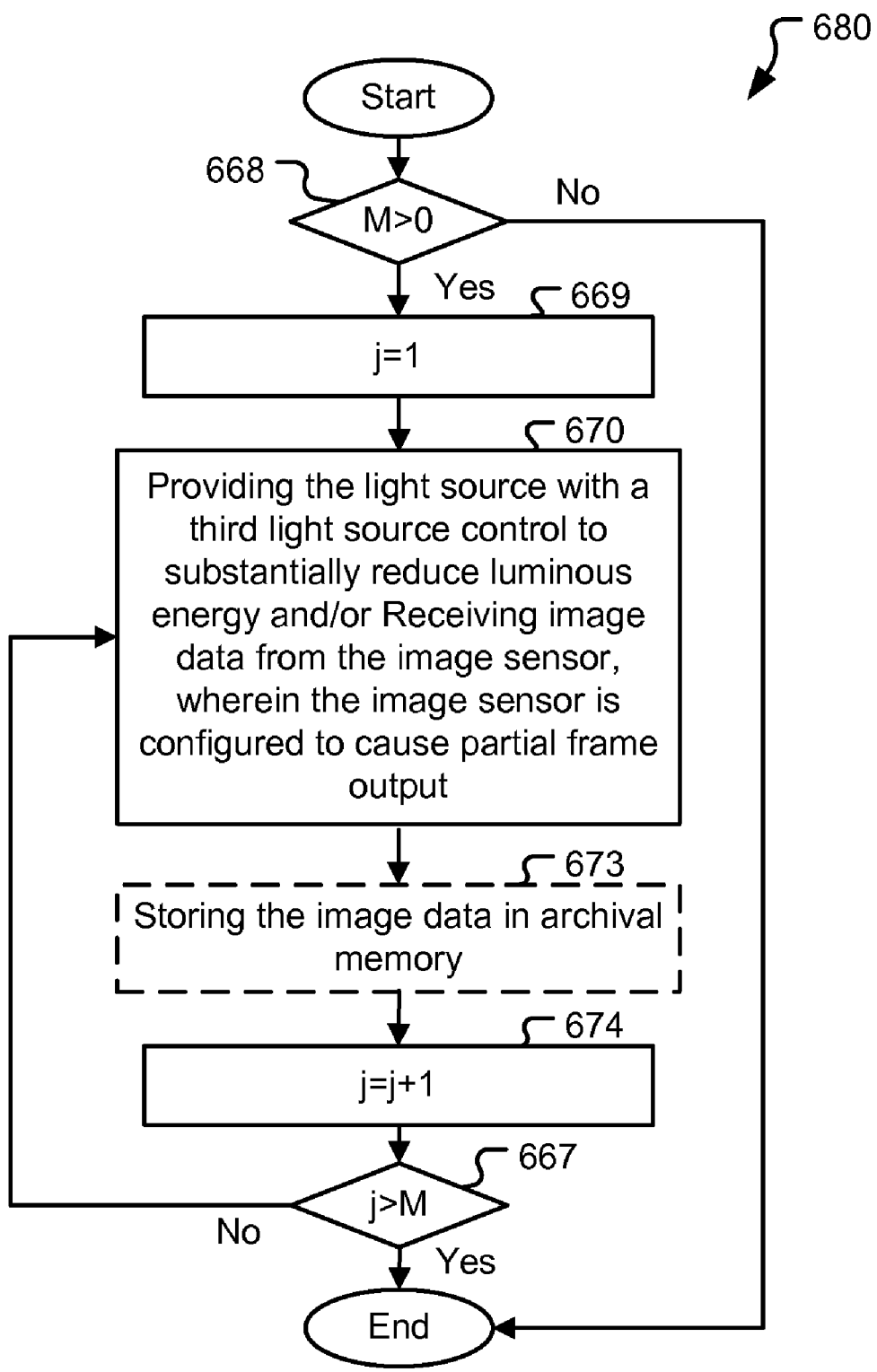
FIG. 6C is a flow chart illustrating an example of routine for processing M frames in the Conservation Mode according to one embodiment.

The capture routine is shown in FIG. 6B for capturing (N−1) frames, since one frame is already captured in step 620 and stored in step 655. To start the iteration, the index i is set to 1 as shown in block 657. A second light source control is applied to the light source to illuminate lumen walls in step 661. The image data is received from the image sensor in step 662 and the image data is stored in the archival memory in step 665. The index i is then incremented in block 666 and a test "i>(N−1)?" is done in step 667. If the condition is satisfied, the routine is complete. Otherwise, the process goes to step 660. If capturing N frames is desired, the block 656 is skipped and the testing of "i>(N−1)" in block 667 is modified to "i>N?". The Conservation Mode routine is shown in FIG. 6C, where the mode is applied to M frames and M is an integer greater than or equal to zero. The testing "M>0?" is performed in step 668. If the condition is false, the process goes to End. Otherwise the iteration starts by setting "j=1" in step 669. A third light source control is applied to the light source to substantially reduce the luminous energy in step 670, where the substantial luminous energy reduction is in reference to the full luminous energy. In one example, the light source may be configured to provide a fixed very-low luminous energy in the Conservation Mode. Substantially reducing the luminous energy also includes the case of turning off the light source. The incoming image data is received in step 672, wherein the image sensor is configured to cause partial frame output, where partial frame output could mean no output, and the incoming image is then stored in archival memory as shown in step 673. The index j is then incremented in step 674 and the testing "j>M?" is performed in step 667. If the condition is satisfied, the routine goes to End and otherwise the routine goes back to step 670.

While the example illustrated in FIG. 6A always includes step 620 to receive image data from the image sensor and to buffer the image data in buffer memory, alternative methods can also be used. For example, when the operation returns from step 680 corresponding to the Conservation Mode, there is a higher possibility that the next frame may have no motion. Therefore, in light of the anticipation that the next frame may not have to be stored in the archival storage, the full-frame image data will not be buffered in the buffer memory upon the return from the Conservation Mode. Also, in this case, the light source control may produce an illumination level similar to that used in conservation mode and lower than that in capture mode.

Figure 6D:
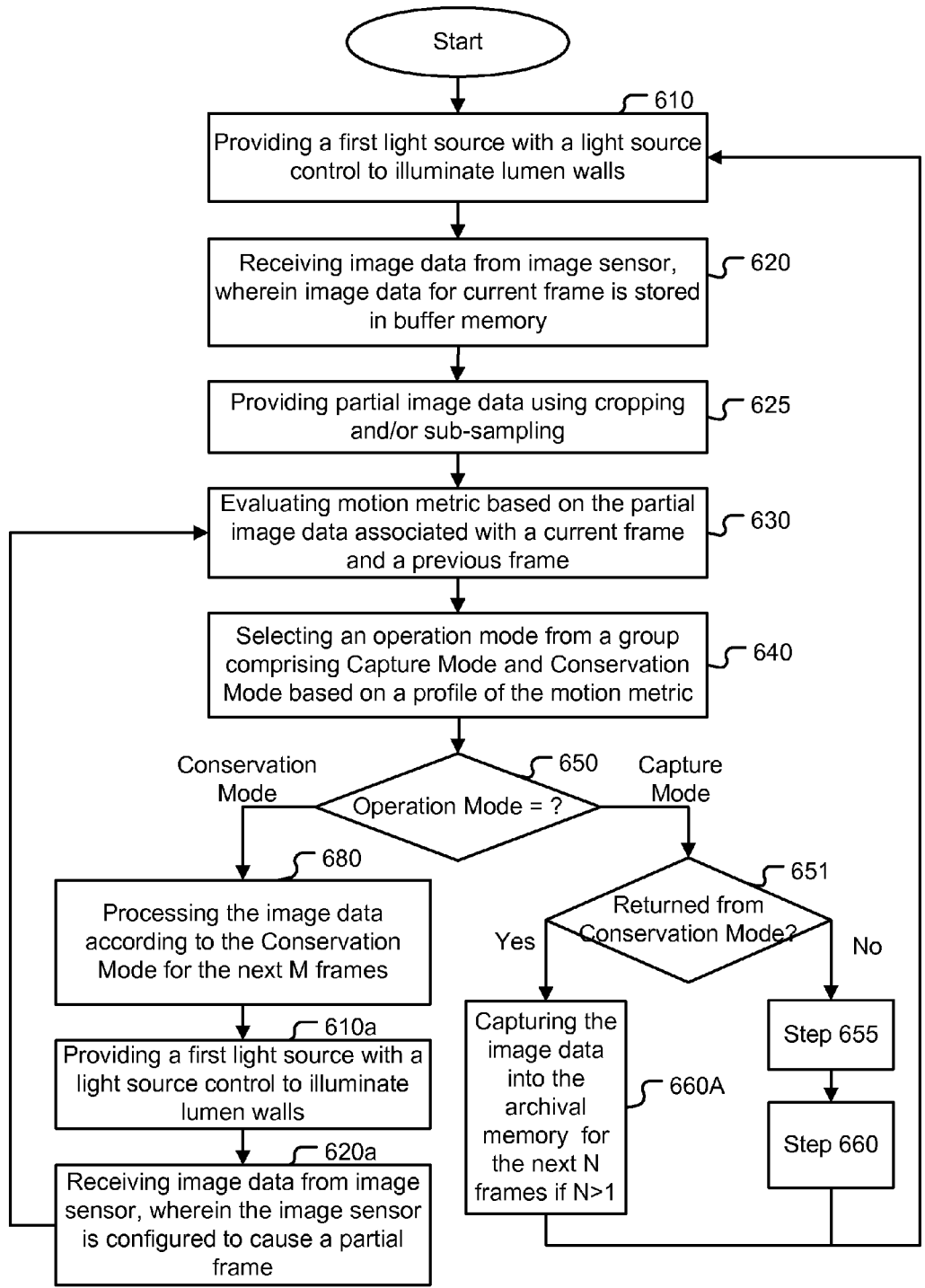
FIG. 6D is a flow chart illustrating an example of capture control operation according to another embodiment, wherein an image cropping/spatial sub-sampling module is used.

As mentioned previously that the Motion Assessment phase may dynamically adjust settings depending on previous mode. For example, if the previous mode is Conservation Mode, the Motion Assessment phase may be configured to cause the image sensor to provide partial frame instead of full frame. In this case, only a partial frame corresponding to the current frame is available in the current frame buffer. If the system chooses Capture Mode based on a profile of the motion metric, a full current frame will not be available. Therefore, the system has to bypass the step 655 of FIG. 6A. Instead, the system has to set up the image sensor properly to output a full frame image and capture the next frame. FIG. 6D illustrates an example of flowchart according to an alternative embodiment of the present invention, where the steps 610a and 620a for Conservation Mode will prepare the partial image for motion assessment purpose. If Capture Mode is select, the system will check whether the process returned from a previous Conservation Mode as shown in step 651. If a "Yes" is asserted, the process will execute step 660A which is similar to the step 660 except that it captures N frames instead of (N−1) frame since there is no step 655 for the first frame to be captured. If a "No" is asserted in the test of step 651, the process flow will store the first frame in step 655 and capture the remaining (N−1) frame into archive memory.

Figure 7:
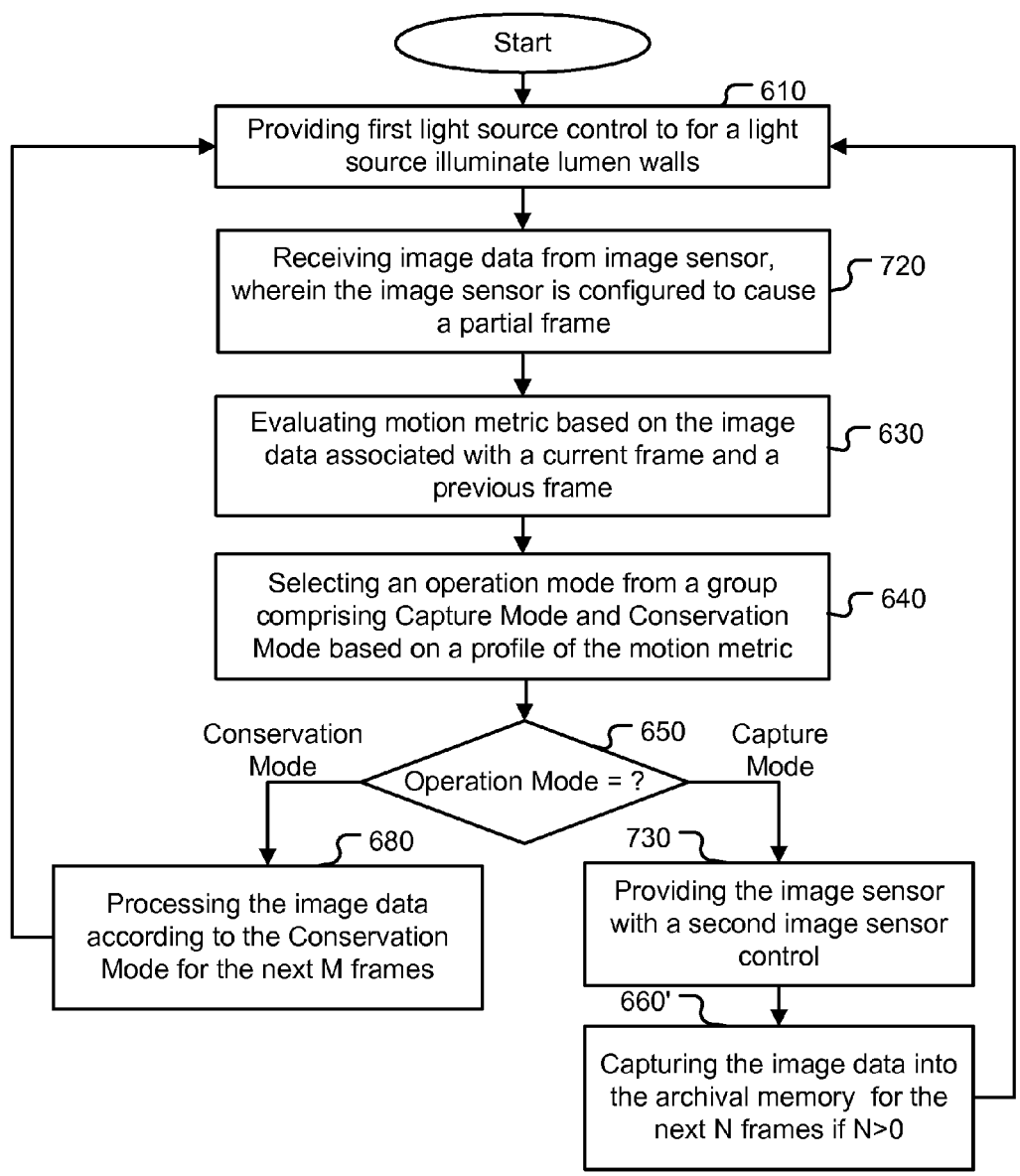
FIG. 7 is a flow chart illustrating an example of capture control operation according to another embodiment, wherein the image sensor is configured to cause partial frame output during the Motion Assessment phase.

FIG. 7 illustrates an exemplary flowchart corresponding to the operation of capsule control processing module 17A in FIG. 3. The flowchart is substantially the same as that in FIG. 6A and the same reference numeral will be assigned to the block performing the same function. The steps 610, 720, 630 and 640 correspond to the Motion Assessment phase of FIG. 5. Instead of reducing the image size using cropping and/or spatial sub-sampling in step 625, the capsule control processing module provides the image sensor with a image sensor control to cause partial frame output from the image sensor as shown in step 720. In the Capture Mode, a second image sensor control is applied to the image sensor as shown in step 730. Since the first image sensor control will cause the image size substantially reduced and the Capture Mode desires high quality capture of the incoming image, the second image sensor control is needed to select a full image resolution as desired. After the second image sensor control is applied in step 730, the light source is applied in step 661. The image data is then received in step 662 and stored in the archival memory in step 665. In the Capture Mode, since the image data for the current frame is not available, the step 655 of FIG. 6A is not performed. If the operation mode is Conservation Mode, the routine 680 is followed to process the next M frames, where M is an integer greater than or equal to zero.

Figure 8A:
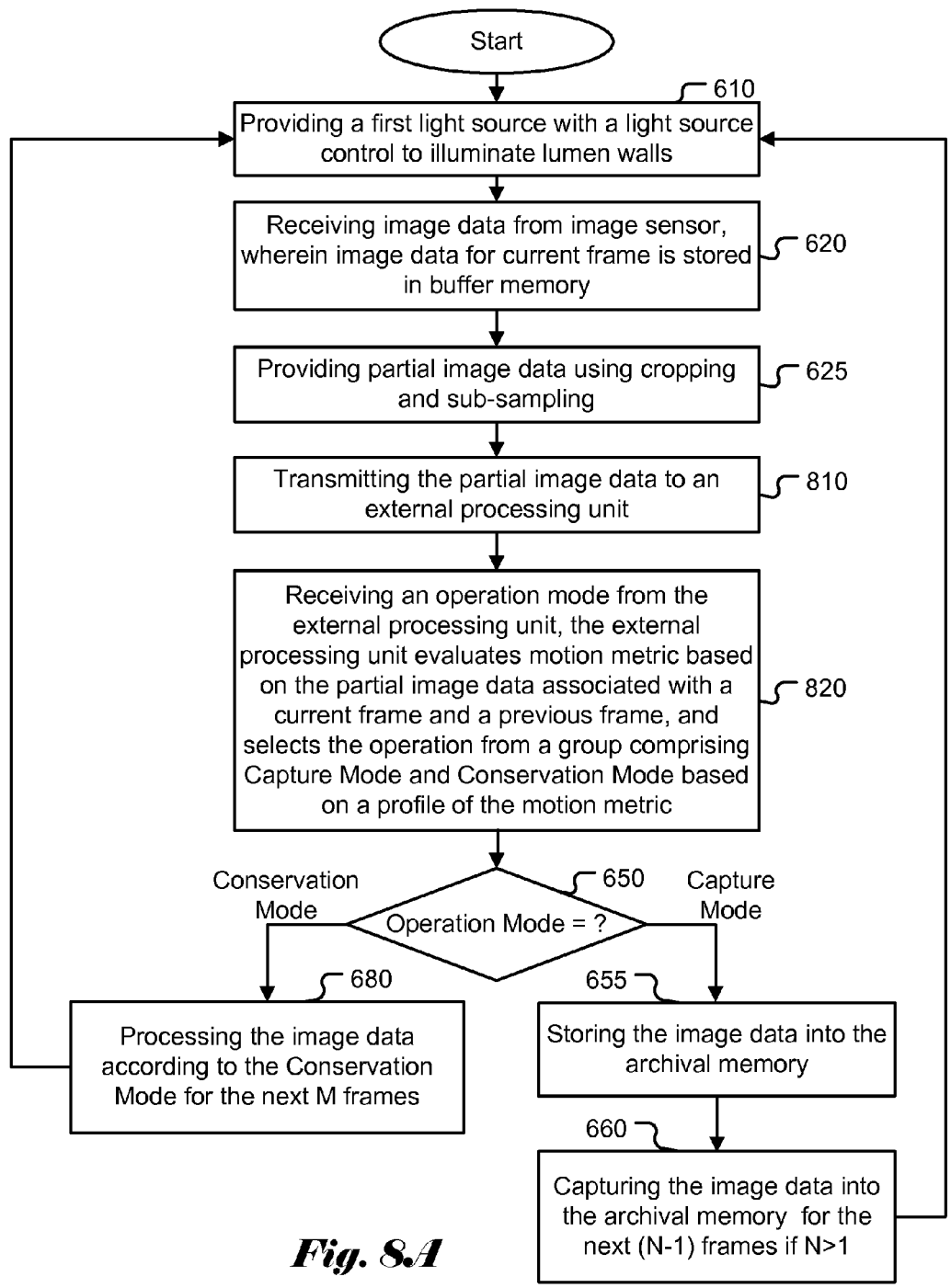
FIG. 8A is a flow chart illustrating an example of capture control operation according to one embodiment, wherein an image cropping/spatial sub-sampling module is used to provide partial frame for motion evaluation and the motion evaluation is done by an external processing unit.
Figure 8B:
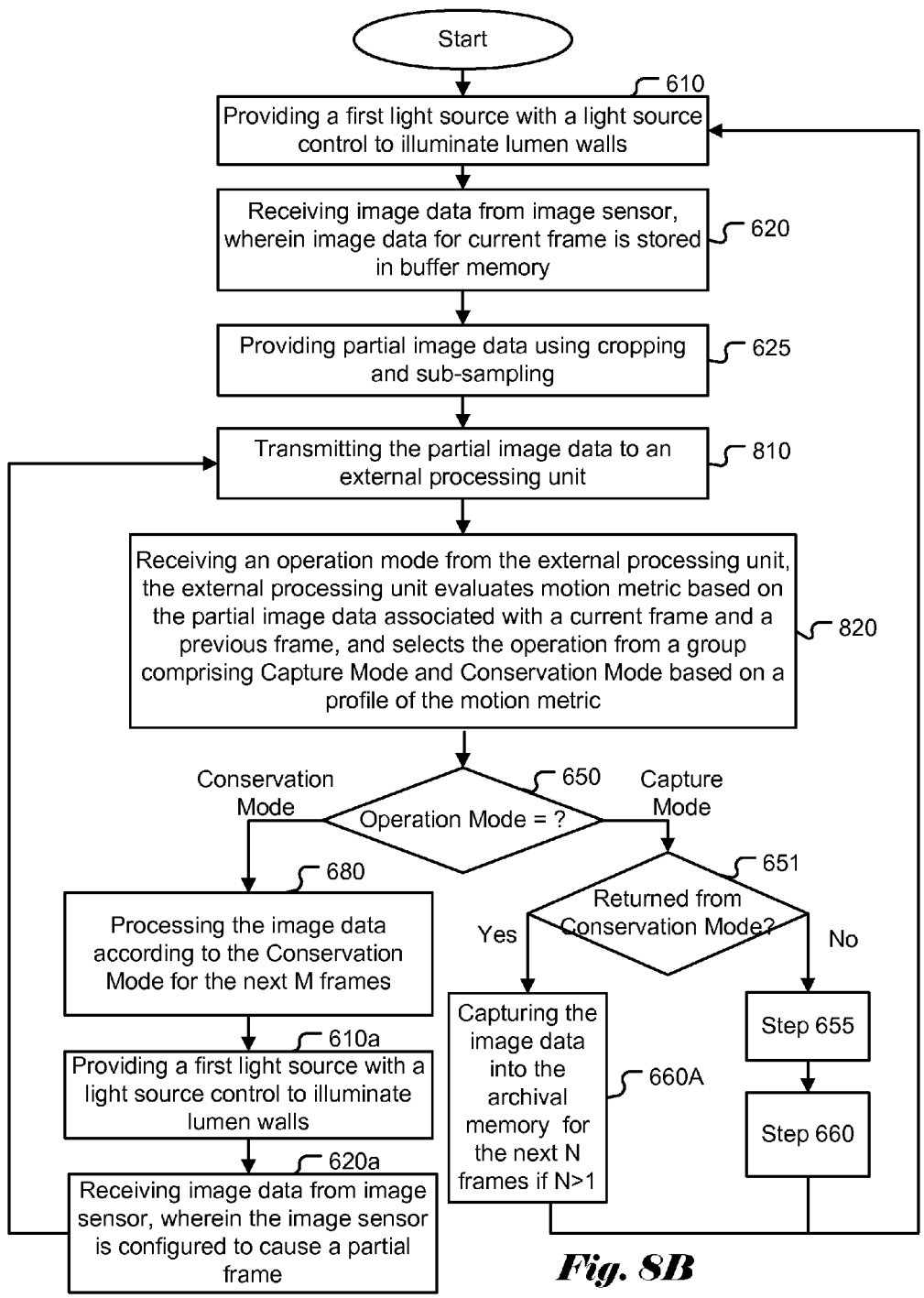
FIG. 8B is a flow chart illustrating an example of capture control operation according to another embodiment, wherein an image cropping/spatial sub-sampling module is used to provide partial frame for motion evaluation and the motion evaluation is done by an external processing unit.

FIG. 8A illustrates a detailed exemplary flowchart for the operation of capsule control processing module 17B in FIG. 4A, wherein an external processing unit is incorporated to evaluate the motion metric and determine an operation mode. The flowchart is substantially the same as that in FIG. 6A and the same reference numeral will be assigned to the block performing the same function. The steps 610 through 625, 810 and 820 correspond to the Motion Assessment phase of FIG. 5. The partial image data using cropping and spatial sub-sampling in step 625 is transmitted to the external processing unit in step 810. The external processing unit will evaluate the motion metric based on the partial image data associated with a current frame and a previous frame, and selects the operation from a group comprising Capture Mode and Conservation Mode based on a profile of the motion metric. The capsule control processing module then receives the operation mode from the external processing unit in step 820. When the operation is available, the remaining processing steps in FIG. 8 are the same as those in FIG. 6A. Storing the image data in archival memory may include transmitting it to an external receiver. FIG. 8B illustrates an example of flowchart according to an alternative embodiment of the present invention similar to FIG. 8A, where the sensor will output partial frame image upon return from Conservation Mode. If the system selects Capture Mode based on a profile of the motion metric, it has to test whether it returned from Conservation Mode to take respective actions as shown in FIG. 8B.

Figure 9:
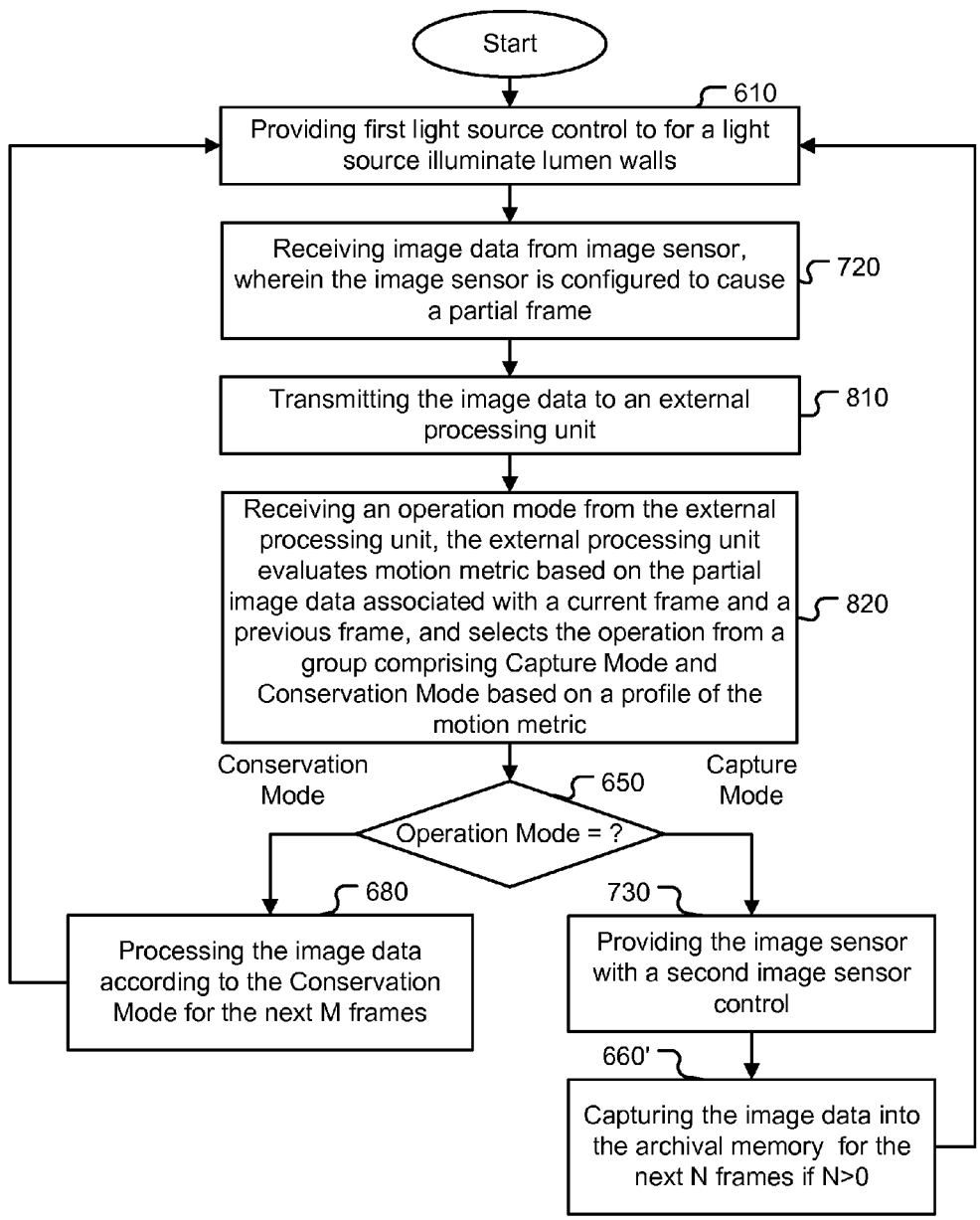
FIG. 9 is a flow chart illustrating an example of capture control operation according to another embodiment, wherein the image sensor is configured to cause partial frame output during the Motion Assessment phase.

FIG. 9 illustrates a detailed exemplary flowchart for the operation of capsule control processing module 17C in FIG. 4B, wherein an external processing unit is incorporated to evaluate the motion metric and determine an operation mode. The flowchart is substantially the same as that in FIG. 7 and the same reference numeral will be assigned to the block performing the same function. The steps 610, 720, 810 and 820 correspond to the Motion Assessment phase of FIG. 5.

The above detailed description illustrates the specific embodiments of the present invention and is not intended to be limiting. Numerous modifications and variations within the scope of the invention are possible. The present invention is set forth in the following claims.

The invention claimed is:

1. A method for capsule camera control, the method comprising:
    (a) providing a light source with a first light source control to illuminate lumen walls;
    (b) receiving image data from an image sensor of a capsule camera to derive a first frame;
    (c) evaluating a motion metric, associated with the first frame and a previously captured frame, based on motion vectors, SAD, MSE, total variance, center of mass, count of pixels having large differences or count of zero-valued motion vectors; and
    (d) selecting an operation mode for next image data from a group comprising Capture Mode and Conservation Mode based on a profile of the motion metric, wherein the Capture Mode is selected if the profile indicates an amount of motion between the first frame and the previously captured frame exceeding a threshold and the Conservation Mode is selected otherwise, and wherein a current image data is buffered in substantially reduced resolution and/or substantially reduced size if the mode is the Conservation Mode;
    wherein steps (a) through (d) are performed inside a capsule camera.

2. The method of claim 1, wherein said evaluating motion metric is based on a portion of the first frame and a portion of the previously captured frame.

3. The method of claim 2, wherein the portion of the first frame is caused by configuring the image sensor.

4. The method of claim 2, wherein the portion of the first frame is caused by processing the received image data using a processing module.

5. The method of claim 1, wherein the operating mode is stored in storage selected from a group comprising a first memory in the capsule camera and a second memory outside the capsule camera.

6. The method of claim 1, wherein the Capture Mode further comprising:
(e) storing a full resolution and full size frame derived from the next image data in an archival memory selected from a group consisting of memory inside the capsule camera and memory external to the capsule camera.

7. The method of claim 1, wherein the Capture Mode further comprising:
(f) receiving the next image data from the image sensor to derive a new current frame;
(g) evaluating second motion metric associated with the new current frame and the previously captured frame;
(h) selecting a new operation mode for the frame following the new current frame based on a profile of the second motion metric, wherein the Capture Mode is selected if the profile indicates the amount of motion between the new current frame and the previously captured frame exceeds a second threshold and the Conservation Mode is selected otherwise; and
(i) storing the frame following the new current frame in full-size and full-resolution frame derived in archival memory if the new operation mode is the Capture Mode.

8. The method of claim 7, wherein the Capture Mode further comprising:
(j) discarding the next image data if the new operation mode is the Conservation Mode.

9. The method of claim 7, wherein the next image data is buffered in a buffer memory in a compressed format.

10. The method of claim 7, wherein the Conservation Mode further comprising:
(k) a processing step selected from a group comprising:
(i) configuring the image sensor to cause the image sensor not to output the next image data;
(ii) receiving the next image data from the image sensor and discarding the next image data; and
(iii) receiving the next image data from the image sensor and storing the next image data in reduced size and/or resolution.

11. The method of claim 10, wherein the Conservation Mode further comprising:
(l) configuring the image sensor to cause reduced image size and/or resolution for the next image data before said receiving the next image data from the image sensor.

12. The method of claim 7, wherein the Conservation Mode further comprising:
(m) providing the light source with a second light source control to substantially reduce luminous energy.

13. The method of claim 12, wherein the first light source control and the second light source control include multiplicative luminous energy control.

14. The method of claim 1, wherein the profile of the motion metric comprises motion matrices corresponding to a current frame and at least one prior frame.

15. A capsule camera apparatus, comprising:
an image sensor, within the capsule camera, to provide image data;
a processing module, within the capsule camera, to derive a first frame and a second frame from the image data;
a motion evaluation module, within the capsule camera, to measure a motion metric based on the first frame and a previously captured frame, the motion metric being based on motion vectors, SAD, MSE, total variance, center of mass, count of pixels having large differences or count of zero-valued motion vectors;
an archival memory to store a frame according to an archival control;
a decision module, within the capsule camera, to select an operation mode for the second frame from a group comprising Capture Mode and Conservation Mode based on a profile of the motion metric, wherein the Capture Mode is selected if the profile indicates an amount of motion between the first frame and the previously captured frame exceeding a threshold and the Conservation Mode is selected otherwise, and wherein a current image data is buffered in substantially reduced resolution and/or substantially reduced size if the mode is the Conservation Mode; and
a controller, within the capsule camera, to provide the archival control based on the operation mode selected.

16. The capsule camera apparatus of claim 15, wherein if the Capture Mode is selected for the second frame:
the motion evaluation module is configured to evaluate a second motion metric associated with the second frame and a second previously captured frame; and
the controller is configured to cause the second frame to be stored in full size and full resolution if a profile of the second motion metric indicates an amount of motion between the second frame and the second previously captured frame exceeding a second threshold.

17. The capsule camera apparatus of claim 16, wherein the controller is configured to cause the second frame to be discarded if the profile of the second motion metric indicates the amount of motion between the second frame and the second previously captured frame not exceeding the second threshold.

18. The capsule camera apparatus of claim 15, wherein, if Conservation Mode is selected for the second frame, the controller provides the archival control to either cause the second frame to be stored in the archival memory in reduced size and/or reduced resolution or cause the second frame not to be stored in archival memory.

19. The capsule camera apparatus of claim 15, wherein the motion evaluation module measures the motion metric based on a portion of the first frame and a portion of the previously captured frame.

20. A capsule camera apparatus, comprising:
an image sensor, within the capsule camera, to provide image data, wherein image size and/or resolution can be adjusted according to a sensor control applied to the image sensor;
a motion evaluation module, within the capsule camera, to measure a motion metric based on a first frame associated with the image data and a previously captured frame, the motion metric being based on motion vectors, SAD, MSE, total variance, center of mass, count of pixels having large differences or count of zero-valued motion vectors;
a decision module, within the capsule camera, to select an operation mode for a second frame associated with the image data from a group comprising Capture Mode and Conservation Mode based on a profile of the motion metric, wherein the Capture Mode is selected if the profile indicates an amount of motion between the first frame and the previously captured frame exceeding a threshold and the Conservation Mode is selected otherwise, and wherein the sensor control causes the image sensor to output substantially resolution-reduced and/or substantially size-reduced image data if the mode is the Conservation Mode; and a controller, within the capsule camera, to provide the sensor control based on the operation mode selected.

21. The capsule camera apparatus of claim 20, wherein, if the Conservation Mode is selected for the second frame, the controller provides the sensor control to the image sensor to either cause the image sensor to output the image data in reduced size and/or reduced resolution to form the second frame or to cause the image sensor not to output the image data to form the second frame.

22. The capsule camera apparatus of claim 20, wherein the motion evaluation module measures the motion metric based on a portion of the first frame and a portion of the previously captured frame.

\* \* \* \* \*